United States Patent [19]

Tartacower et al.

[11] Patent Number: 5,606,981
[45] Date of Patent: Mar. 4, 1997

[54] CATHETER GUIDEWIRE WITH RADIOPAQUE MARKERS

[75] Inventors: Richelle Tartacower, Atkinson; Lex Jansen, Londonderry, both of N.H.; Joanne Gilbert, Amesbury, Mass.; Rebecca C. Testa, Nashua, N.H.

[73] Assignee: C. R. Bard, Inc., Murray Hill, N.J.

[21] Appl. No.: 383,322

[22] Filed: Feb. 3, 1995

Related U.S. Application Data

[63] Continuation-in-part of Ser. No. 212,558, Mar. 11, 1994, abandoned.

[51] Int. Cl.⁶ ........................................................ A61B 5/00
[52] U.S. Cl. ............................................. 128/772; 128/657
[58] Field of Search ...................................... 128/657, 654, 128/658, 772; 604/95, 96, 280, 281

[56] References Cited

U.S. PATENT DOCUMENTS

| | | |
|---|---|---|
| Re. 33,911 | 5/1992 | Samson . |
| 3,757,768 | 9/1973 | Kline ...................................... 128/657 |
| 4,279,252 | 7/1981 | Martin . |
| 4,456,017 | 6/1984 | Miles . |
| 4,538,622 | 9/1985 | Samson et al. . |
| 4,545,390 | 10/1985 | Leary . |
| 4,619,274 | 10/1986 | Morrison . |
| 4,721,117 | 1/1988 | Mar et al. . |
| 4,757,827 | 7/1988 | Buchbinder et al. . |
| 4,763,647 | 8/1988 | Gambale ................................. 128/657 |
| 4,796,637 | 1/1989 | Mascuch et al. . |
| 4,798,598 | 1/1989 | Bonello et al. . |
| 4,815,478 | 3/1989 | Buchbinder et al. . |
| 4,821,722 | 4/1989 | Miller et al. . |
| 4,846,186 | 7/1989 | Box et al. . |
| 4,867,174 | 9/1989 | Skribiski . |
| 4,873,983 | 10/1989 | Winter . |
| 4,884,579 | 12/1989 | Engelson . |
| 4,895,168 | 1/1990 | Machek . |
| 4,922,924 | 5/1990 | Gambale et al. . |
| 4,957,110 | 9/1990 | Vogel et al. . |
| 5,040,543 | 8/1991 | Badera et al. . |
| 5,063,935 | 11/1991 | Gambale . |
| 5,065,769 | 11/1991 | de Toledo . |
| 5,069,217 | 12/1991 | Fleischhacker, Jr. . |
| 5,084,022 | 1/1992 | Claude . |

(List continued on next page.)

FOREIGN PATENT DOCUMENTS

| | | |
|---|---|---|
| 519604 | 12/1992 | European Pat. Off. . |
| WO9219151 | 11/1992 | WIPO . |
| WO9319663 | 10/1993 | WIPO . |

*Primary Examiner*—Max Hindenburg
*Assistant Examiner*—Pamela Wingood
*Attorney, Agent, or Firm*—Bookstein & Kudirka, P.C.

[57] ABSTRACT

A guidewire for use with a catheter has varying radiopacity as well as at least one radiopaque marker in its distal end. In one embodiment, the guidewire includes a shaft that supports a distal radiopaque coil and a proximal radiopaque coil. The proximal and distal coils are spaced apart from one another. The non-radiopaque area between the two coils has at least one radiopaque marker band attached to the shaft. The marker bands provide several radiographically visible reference Lengths. A polymer sleeve encases the marker bands and the shaft between the first and second coils providing a uniform outer diameter to the distal region of the guidewire. In another embodiment, the proximal coil may be omitted. In a further embodiment, a radiopaque coil having varying pitch along its length is supported by and attached to a distal region of the core wire. The coil includes highly radiopaque distal and proximal sections, or highly radiopaque distal section and lightly radiopaque window section, and a more moderately radiopaque intermediate section. The intermediate section of the coil may include at least one smaller tightly wound radiographically dark coil section separated from the distal and proximal sections and from one another by loosely wound coil sections. A polymer sleeve is attached to the guidewire and covers a portion of the coil. In a fourth embodiment, the sleeve is attached to the guidewire only at its ends and covers the intermediate window section of the coil.

11 Claims, 5 Drawing Sheets

U.S. PATENT DOCUMENTS

| | | |
|---|---|---|
| 5,095,915 | 3/1992 | Engelson . |
| 5,129,890 | 7/1992 | Bates et al. . |
| 5,144,959 | 9/1992 | Gambale et al. . |
| 5,174,302 | 12/1992 | Palmer . |
| 5,176,149 | 1/1993 | Grenouillet . |
| 5,178,158 | 1/1993 | de Toledo . |
| 5,184,627 | 2/1993 | de Toledo . |
| 5,209,730 | 5/1993 | Sullivan . |
| 5,211,636 | 5/1993 | Mische . |
| 5,228,453 | 7/1993 | Sepetka . |
| 5,253,653 | 10/1993 | Daigle et al. . |
| 5,259,393 | 11/1993 | Corse, Jr. et al. . |
| 5,267,574 | 12/1993 | Viera et al. . |
| 5,409,004 | 4/1995 | Sloan ................................ 128/657 |

CATHETER GUIDEWIRE WITH RADIOPAQUE MARKERS

RELATED APPLICATION

This application is a continuation-in-part of application Ser. No. 08/212,558, filed Mar. 11, 1994 and abandoned.

FIELD OF THE INVENTION

The invention relates to guidewires used to support and guide dilatation catheters as they are advanced through body lumens such as blood vessels.

BACKGROUND OF THE INVENTION

A wide variety of guidewires are used for various medical purposes in the treatment of the human body. Typically guidewires are used to guide a catheter to a site within a patient's blood vessel to perform the procedure for which the catheter is adapted. For example, guidewires, particularly small diameter steerable guidewires, perform the important function in percutaneous transluminal coronary angioplasty of guiding a balloon catheter such that the balloon can be placed at the site of the stenosis (obstruction) to be treated. The balloon is then inflated to dilate the stenosis and subsequently increase the blood flow through the artery.

Typical angioplasty steerable guidewires include a torsionally rigid, longitudinally flexible shaft and a flexible distal end that includes a coil, all or part of which may be radiopaque, so that a physician can monitor fluoroscopically the position and advancement of the guidewire.

During procedures, such as coronary angioplasty, it is often the practice to inject a radiopaque contrast liquid into the artery so that the shape and path of the artery, particularly in the region of the stenosis, may be visualized fluoroscopically. The radiopacity of some guidewire coils may be so dense as to visually obstruct the stenosed part of the artery when the contrast liquid is injected. As a result of the visual obstruction, the ability of the physician to visualize and assess the nature of the stenosis is impaired.

U.S. Pat. No. 5,144,959 (Gambale) describes a guidewire which does not visually obstruct the desired part of the artery when contrast liquid is injected. The distal region of the Gambale guidewire includes a coil having a highly radiopaque distal portion, a moderately radiopaque proximal portion and a non-radiopaque intermediate portion. The guidewire may be advanced so that its distal portion advances through and beyond the stenosis while the non-radiopaque portion is disposed at the region of the stenosis to prevent visual obstruction. The moderately radiopaque proximal portion provides an indication of the position and configuration of the more proximally located portions of the guidewire. Thorough assessment of the stenosis, however, is difficult without the provision of a visual reference length.

The provision of a visible reference length would enable the physician to make in vivo measurements of the lesion to determine its length and shape and dimensions of the artery adjacent to the lesion. The assessment facilitates the selection of an appropriately sized balloon catheter and, additionally, in the event that a stent is needed to prevent the artery from collapsing in the area of the lesion, aids in the selection of an appropriately sized stent. It is, therefore, desirable for the distal region of non-obstructing guidewires to include a highly radiopaque distal section and more proximal uniformly spaced radiopaque markers, which provide such a reference length.

It is among the general objects of the invention to provide guidewires having the foregoing desirable characteristics.

SUMMARY OF THE INVENTION

A guidewire, in accordance with the invention, has an elongate flexible shaft. In a first embodiment of the invention, a distal radiopaque coil is supported about and is attached to a distal portion of the shaft. A proximal radiopaque coil is supported about and is attached to a distal portion of the shaft, spaced proximally from the distal coil. The distal coil may be more radiopaque than the proximal coil which would make it appear darker than the proximal coil under fluoroscopy. The two coils may have identical radiopacity. A polymer sleeve encases the shaft between the distal and proximal coils, its ends overlapping the proximal end of the distal coil and the distal end of the proximal coil. The guidewire also includes at least one radiopaque marker band attached to the shaft between the distal and proximal coils and encased by the polymer sleeve. Thus, the guidewire provides a distal region having a highly radiopaque distal portion, a non-radiopaque intermediate portion (except for the radiopaque markers), and a moderately or highly radiopaque proximal portion.

In a second embodiment of the invention, a radiopaque coil is supported about and is attached to the distal portion of the distal region of the shaft. At least one radiopaque marker band is attached to the proximal portion of the distal region of the shaft. A polymer sleeve encases the marker bands and the proximal portion of the distal region of the shaft. In this embodiment, the guidewire provides a distal region having a highly radiopaque distal portion and a non-radiopaque proximal portion (except for the radiopaque markers).

In a third embodiment of the invention, a radiopaque coil is supported about and is attached to the distal region of the shaft. The coil has varying pitch along its length and includes highly radiopaque distal and proximal sections and a moderately radiopaque intermediate section. The guidewire may also include an additional small radiopaque coil attached to the distal end of the guidewire and located within the distal section of the coil for increased radiopacity in the distal section. The intermediate section may include one or more tightly wound coil sections. Each coil section appears as a dark marker under fluoroscopy, and is separated from the proximal and distal sections by loosely wound coil sections, which appear lighter under fluoroscopy. A polymer sleeve encases the coil along a majority of the length of the coil. Thus, the guidewire provides a distal region having highly radiopaque distal and proximal portions and a very lightly radiopaque intermediate portion (except for the darker radiopaque markers).

In a fourth embodiment of the invention, a radiopaque coil is supported about and is attached to the distal region of the shaft. The coil has varying pitch along its length and includes highly radiopaque distal and proximal sections and a lightly radiopaque intermediate window section. The intermediate window section may include one or more smaller tightly wound coil sections separated by loosely wound coil sections. Each smaller tightly wound coil section appears as a dark marker under fluoroscopy. A polymer sleeve encases the intermediate window section of the coil. The sleeve is attached to the guidewire only at the ends of the sleeve by heat shrinking the ends of the sleeve to the tightly wound coils immediately adjacent the intermediate window section. A small gap exists between the coils of the intermediate window section and the sleeve such that the contour of the coils in the window section do not project through the sleeve. Thus, the guidewire provides a distal region having highly radiopaque distal and proximal portions and a lightly radiopaque intermediate portion (except for the darker radiopaque markers).

The guidewire of the invention is intended to be used such that the non-radiopaque section (if using the guidewire of the first or second embodiments), or lightly radiopaque section (if using the guidewire of the third or fourth embodiments), is placed within the stenosed region of the artery so that the radiopacity of the guidewire will not interfere with the fluoroscopic imaging of the stenosis when the artery is injected with radiopaque contrast liquid. The radiopaque markers provide a reference for the physician to measure the length of the stenosis, the dimensions of the adjacent arterial area, and/or to mark the location of a lesion or a stent. Thus, the markers aid in the selection of an appropriate balloon and, if necessary, in the selection of an appropriate stent. This invention allows the physician to do this regardless of visualization angle or degree of fluoroscopic magnification. The polymer sleeve insulates the spaced coils or bands from the inner arterial wall and provides a uniform outer diameter (in some embodiments) to the distal region of the guidewire such that a catheter will smoothly move over the guidewire.

DESCRIPTION OF THE DRAWINGS

The foregoing and other objects and advantages of the invention will be appreciated more fully from the following further description thereof, with reference to the accompanying drawings wherein.

It is to be appreciated that the figures are not drawn to scale and are highly diagrammatic to illustrate the concepts of the invention.

DESCRIPTION OF THE ILLUSTRATIVE EMBODIMENT

Figure 1:
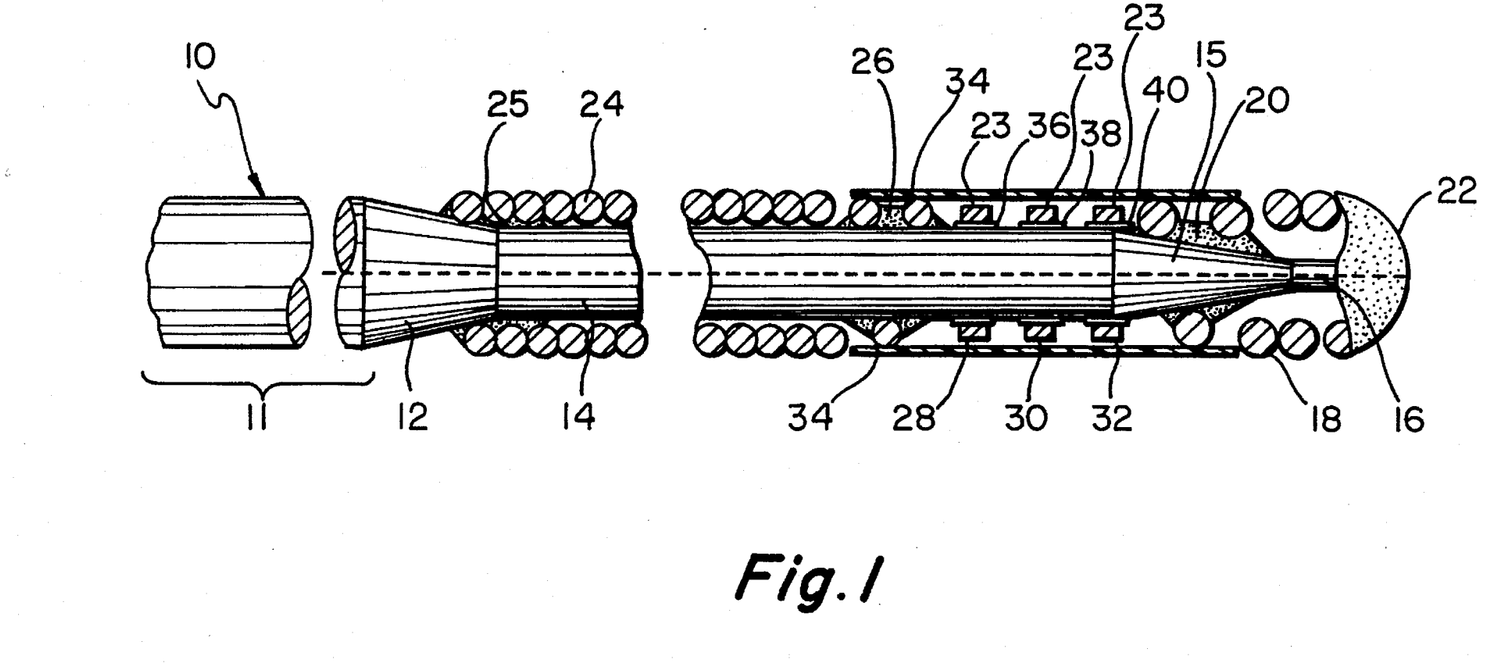
FIG. 1 is a longitudinal sectional fragmented illustration of first embodiment of the invention.

FIG. 1 shows a first embodiment of the invention. As shown, the guidewire, when intended for percutaneous transluminal coronary angioplasty may be approximately 175 cm to 300 cm in total length and includes an elongated rotationally rigid, longitudinally flexible core wire 10, preferably made of stainless steel or other material suitable for use as a guidewire shaft. The majority of the length (approximately 148 cm to 273 cm) is in the proximal segment 11 of the core wire which has a substantially uniform diameter of approximately 0.010" to 0.018". The proximal segment 11 merges into a first tapered segment 12, about 3 cm long which, in turn, merges into an intermediate barrel segment 14, approximately 22.5 cm long and about 6 mils in diameter. Intermediate segment 14 merges into a second tapered segment 15, about 3 cm long which, in turn, merges into a distal barrel segment 16, about 2.5 cm long and approximately 2 mils in diameter. The distal segment 16 is more flexible than the intermediate segment 14. Alternatively, the core wire (from taper 12 to distal segment 16) may have a continuous taper along its length.

A distal coil 18, approximately 3 cm in length, is supported about the distal segment of the core wire and preferably is attached at its proximal end to the core wire by adhesive at joint 20. Suitable adhesives include an ultraviolet curable adhesive or a cyanoacrylate adhesive. The joint 20 alternatively may be welded, soldered or brazed. The distal coil 18 is attached at its distal end to the core wire by a distal hemispherical tip weld 22. The distal coil may be formed from a highly radiopaque material such as a gold/platinum or platinum/tungsten alloy. In a guidewire intended for use in percutaneous transluminal coronary angioplasty, the diameter of the wire from which the distal coil 18 is wound preferably is within the range of 0.001–0.004 inches. The outer diameter of the distal coil 18 preferably is within the range of 0.010–0.018 inches.

A proximal coil 24 is supported about the intermediate segment 14 of the core wire and is preferably attached at its distal end to the core wire by adhesive at joint 26. The proximal end of coil 24 extends to the proximal end of the intermediate segment 14 of the core wire where it may be attached to the core wire by adhesive at joint 25. Joints 25 and 26 may alternatively be welded, soldered or brazed. The outer diameter of the proximal coil is preferably the same as that of the distal coil 18. The proximal coil preferably is 7–22 cm in length. The proximal coil 24 may be less radiopaque than the distal coil 18 or of equivalent radiopacity. The proximal coil preferably is formed from the same material as the distal coil but may be formed from smaller diameter wire to achieve the desired reduced radiopacity.

The region of the guidewire between the proximal and distal coils, including a portion of the intermediate segment 14 and tapered segment 15, is covered by a flexible polymeric sleeve 34. The sleeve, preferably having an outer diameter equal to that of the proximal and distal coils, provides a uniform outer diameter to the distal region of the guidewire such that the catheter will smoothly move over the guidewire during advancement. The sleeve preferably is flexible, kink resistant and includes a lubricious surface for aiding in guidewire maneuverability. The sleeve preferably is formed from a polymer material (such as polyamide or polyethylene) which exhibits the above properties. A hydrophilic or hydrophobic coating may be used to coat the outer surface of the polymer sleeve for added lubricity.

The sleeve preferably is as thin as is practical, depending on the polymer material from which the sleeve is made, in order that the region of the sleeve displays a desired degree of flexibility. The wall thickness of the sleeve preferably falls within the range of 0.0002–0.002 inches. The sleeve preferably covers the proximal end of the distal coil and the distal end of the proximal coil and may be 5–20 cm in length. As shown in FIG. 1, the distal end of the proximal coil 24 and the proximal end of the distal coil 18 can be stretched and tapered down to a smaller diameter in the region where they are attached to the core wire and overlapped by the ends of the polymer sleeve 34. The polymer sleeve preferably is adhesively attached at both ends to the guidewire. If adhesively attached, a small gap 23 exists between the inner surface of the sleeve and outer surfaces of the marker bands 28, 30 and 32 (discussed below). The size of the gap is approximately equal to 0.001 inches but would depend on the thickness of the sleeve wall and the outer diameter of the marker bands. The gap prevents the outer contour of the marker bands from projecting through the polymer sleeve. Alternatively, the sleeve may be heat shrunk about the guidewire.

Radiopaque marker bands 28, 30 and 32 are attached to the core wire between the proximal and distal coils. Marker bands 28, 30 and 32 preferably are attached by adhesive at joints 36, 38 and 40, respectively. Alternatively, joints 36, 38 and 40 may be welded or brazed. The marker bands preferably are made from a radiopaque material such as tantalum, platinum, gold or alloys thereof. The marker bands will be spaced to provide optimum usability for various in vivo dimension measurements by a physician. Particularly, the spacing and dimensions of the marker bands provide reference lengths such that the length and shape of a lesion and adjacent arterial dimensions can be determined fluoroscopically. Such a determination can aid a physician in the selection of an appropriately sized balloon. Additionally, if necessary, such a determination aids in the selection of an appropriately sized stent. The marker bands also provide reference locations which can aid in placing a post-stent balloon after stent placement. While the guidewire preferably includes three marker bands, as shown and described, it is envisioned that as few as one marker band could be used.

The guidewire of the first embodiment thus has a distal tip section 16 that is highly radiopaque, an intermediate section (between the coils) that is non-radiopaque (except for the marker bands), and a proximal section that is moderately or highly radiopaque. Such an arrangement may be referred to as "grey/white/black" or "black/white/black" (from the proximal to the distal ends), referring to its relative appearance under fluoroscopy. The highly radiopaque distal segment provides clear, visible, fluoroscopic indication of the distal tip of the guidewire to indicate clearly the guidewire position. Typically, the distal tip of the guidewire is advanced through and beyond the stenosis to be treated. The intermediate, non-radiopaque segment is intended to be disposed at the region of the stenosis so that the region will be unobstructed by radiopaque effects of the guidewire. Thus, the full radiopaque effect of the radiopaque contrast liquid injected into the artery can be visualized on the fluoroscope, particularly in the critical stenosed region of the artery. The moderately or highly radiopaque proximal segment provides an indication of the position and configuration of the more proximally located portions of the guidewire and, therefore, the proximal arterial anatomy.

The "grey/white/black" or "black/white/black" configuration can be achieved with the appropriate relative degrees of radiopacity by varying the thicknesses of the wires from which the coils are wound, as described above. Alternatively, as will be understood by those skilled in the art, the coils may be plated with varying thicknesses of radiopaque material to achieve the desired levels of radiopacity. The plating process is described in U.S. Pat. No. 5,144,959 (Gambale), which is herein incorporated by reference in its entirety.

Figure 2:
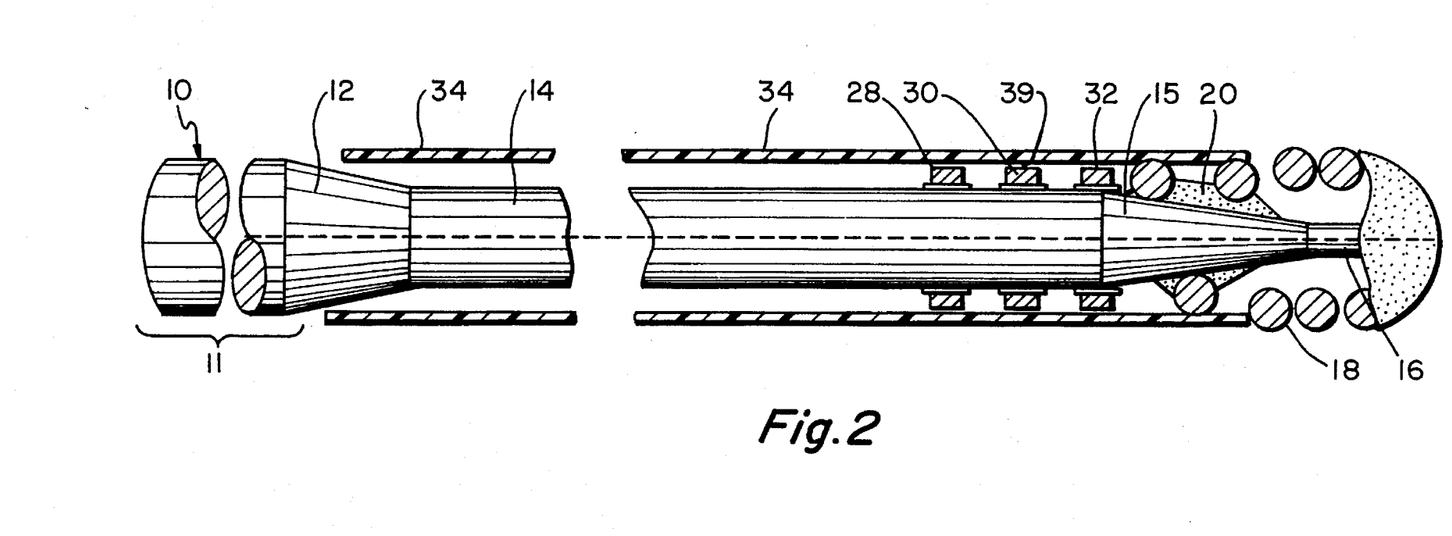
FIG. 2 is a longitudinal sectional fragmented illustration of a second embodiment of the invention.

FIG. 2 illustrates a second embodiment of the invention which is fairly similar in construction to the first embodiment. Like elements in FIG. 2 are referred to by identical reference characters (to those in FIG. 1). In the embodiment of FIG. 2, the construction of the core wire 10, the distal coil 18, and the marker bands 28, 30 and 32 is identical to that of the first embodiment (shown in FIG. 1). The guidewire of the second embodiment, however, omits the proximal coil 24 of the first embodiment. As in the first embodiment, a polymeric sleeve 34, having the same properties as those described above, encases the proximal end of the distal coil and the marker bands. In the second embodiment, however, sleeve 34 extends proximally of the marker bands to tapered segment 12 of core wire 10. The sleeve provides a uniform outer diameter to the distal region of the guidewire to aid in smooth advancement of the catheter over the guidewire. The sleeve preferably is adhesively attached at both ends to the guidewire. Like the embodiment of FIG. 1, if adhesively attached, a small gap 39 exists between the inner surface of the sleeve and the outer surface of the marker bands 28, 30 and 32. The gap prevents the outer contour of the marker bands from projecting through the polymer sleeve. Alternatively, the sleeve may be heat shrunk about the guidewire such that, proximally of the marker bands, the sleeve 34 tapers down to fit tightly around the intermediate segment 14 of core wire to create a smooth transition.

The guidewire of the second embodiment thus has a distal region including a distal tip section 16 that is highly radiopaque and a proximal section that is non-radiopaque. Such an arrangement is referred to as "white/black" (from the proximal to the distal ends), referring to its relative appearance under fluoroscopy. As with the embodiment of FIG. 1, the highly radiopaque distal segment provides clear, visible fluoroscopic indication of the distal tip of the guidewire to indicate clearly the guidewire position and the proximal, non-radiopaque segment provides for unobstructed visualization of the stenosis.

Figure 3:
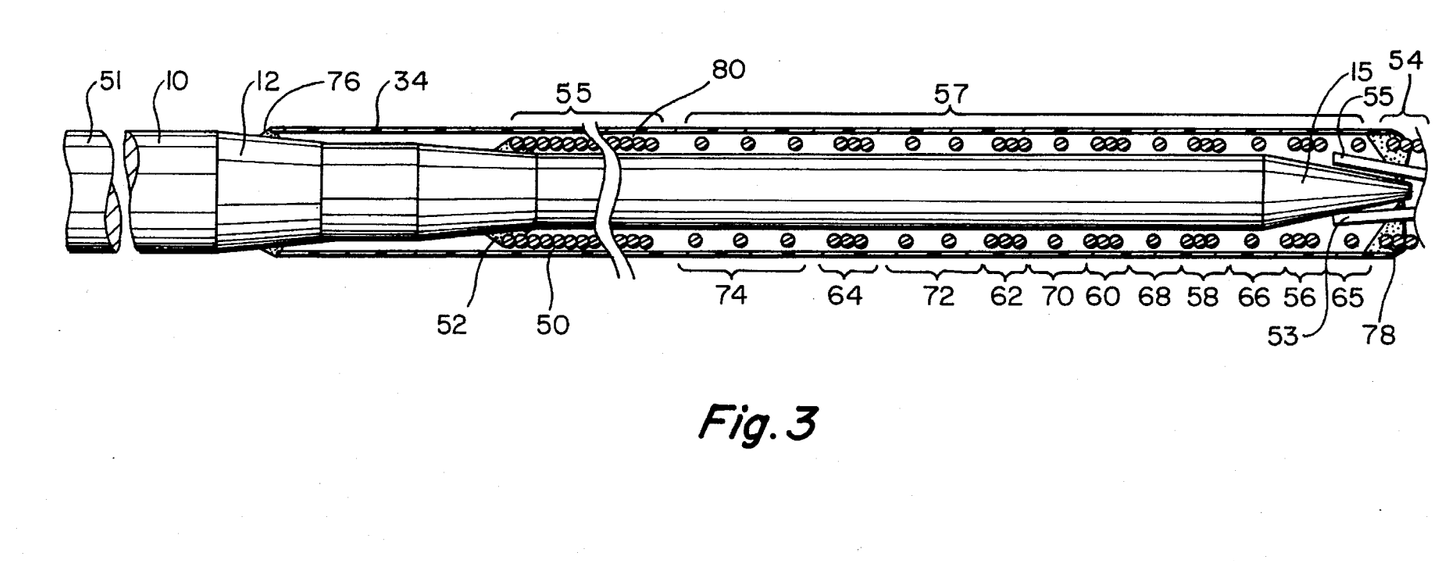
FIG. 3 is a longitudinal sectional fragmented illustration of a third embodiment of the invention.

FIG. 3 shows a third embodiment of the invention in which a radiopaque coil 50 is supported by and attached to a distal region of the core wire 51. Core wire 51 is an alternate embodiment core wire in which the distal barrel segment 16 of the core wire 10 of the first embodiment is absent and is replaced by a pair of round forming wires 53 and 55 which extend from tapered segment 15 to hemispherical tip weld 22. The forming wires, typically 3–7 cm in length, preferably are adhesively attached to tapered segment 15 and extend approximately 2 cm beyond the distal tip of core wire 51. The forming wires preferably are formed from materials such as stainless steel, Sandvik 1RK91, PH455 or MP35N, described below. The forming wires may be round forming wires as disclosed in U.S. application Ser. No. 08/015,642, titled "Guidewire with Round Forming Wires", filed on Feb. 9, 1993, which application is herein incorporated by reference in its entirety. Coil 50 can be used, however, with the core wire 10 of the first embodiment. Similarly, the guidewire constructions of the first and second embodiments can be used with the core wire 51.

As shown in FIG. 3, the distal end of the coil 50 is attached to the hemispherical tip weld and the coil extends proximally to the tapered section 12 of the core wire. The proximal end of the coil 50 is attached to the core wire by adhesive at joint 52. Alternatively, joint 52 may be soldered or brazed. Coil 50 may also be attached to the core wire, preferably by adhesive, near the distal end of the coil to add structural integrity to the distal end of the guidewire such that unwinding of the coil during advancement of the guidewire through an artery is prevented. Spring 50 preferably is formed from a radiopaque material such as a platinum/gold or other suitable alloy. The diameter of the wire from which the coil 50 is wound preferably is within the range of 0.001–0.004 inches. The outer diameter of the coil preferably is within the range of 0.010–0.018 inches. A typical coil length falls within the range of 5–20 cm. If using a coil having a length of 5 cm, the corresponding dimensions of the core wire would be less than that disclosed above, as will be appreciated by those skilled in the art.

Spring 50 has varying pitch along its length including multiple tightly wound coil sections separated by loosely wound coil sections. The tightly wound coil sections appear dark under fluoroscopy and the loosely wound coil sections appear light. Among the tightly wound coil sections are a distal section 54, preferably within the range of 2–3 cm in length, and a proximal section 55, within the range of 3–10 cm in length. Thus, the proximal and distal sections are highly radiopaque.

An intermediate section 57 of the coil may include multiple tightly wound coil sections 56, 58, 60, 62, and 64, and loosely wound coil sections 65, 66, 68, 70, 72, and 74. The intermediate section as a whole appears light under fluoroscopy with the tightly wound sections appearing as dark markers, providing reference lengths and location markers for the physician. Markers 56, 58, 60 and 62 may be uniformly spaced, preferably in 1 cm to 2 cm multiples. The number of markers and the length and spacing thereof, however, can be changed to suit a particular application. It is envisioned, that as few as one marker band could be used.

The majority of the length of the spring, from a proximal point of the distal section to the proximal end of the spring, is covered by a flexible polymeric sleeve 34. Sleeve 34 exhibits the same qualities as the sleeve described above in connection with the first and second embodiments. The sleeve provides a uniform outer diameter to the distal region of the guidewire. The sleeve, therefore, helps to ensure smooth catheter movement over the guidewire during advancement. Sleeve 34 preferably is adhesively attached to the guidewire at proximal 76 and distal 78 joints. If adhesively attached, a small gap 80 exists between the outer surface of spring 50 and the inner surface of sleeve 34. The gap enables free bending movement of the coils of spring 50 beneath the sleeve 34 while the guidewire is maneuvered through an artery. Additionally, the gap prevents the contour of the outer surface of the coils from projecting through the polymer sleeve 34. Alternatively, the ends of the sleeve 34 maybe heat shrunk about the guidewire. It should be understood that the method of attaching the sleeve to the guidewire only at its ends by adhesive or by heat shrinking its ends can be used with any of the guidewire embodiments disclosed herein.

The guidewire of the third embodiment thus has a distal tip section and a proximal section that are highly radiopaque and an intermediate section that is lightly radiopaque (except for the darker markers). Such an arrangement is referred to as "black/grey/black" (from the proximal to the distal ends), referring to its relative appearance under fluoroscopy. As with the previously described embodiments, the highly radiopaque distal segment provides clear, visible fluoroscopic indication of the distal tip of the guidewire to indicate clearly the guidewire position and the intermediate, lightly radiopaque segment provides for substantially unobstructed visualization of the stenosis.

As described above, the proximal and distal sections of the coil preferably are equally highly radiopaque. Alternatively, the distal section can be more radiopaque than the proximal section. To achieve the desired relative radiopacity, the distal section 54 of the coil may be wound from a wire having a greater diameter than that of the proximal section. Alternatively, as will be understood by those skilled in the art, the distal section 54 may include another shorter radiopaque coil 90 which is supported by and attached to the extreme distal part of the core wire and which is located within the distal section of the coil, as shown in FIG. 4.

Figure 4:
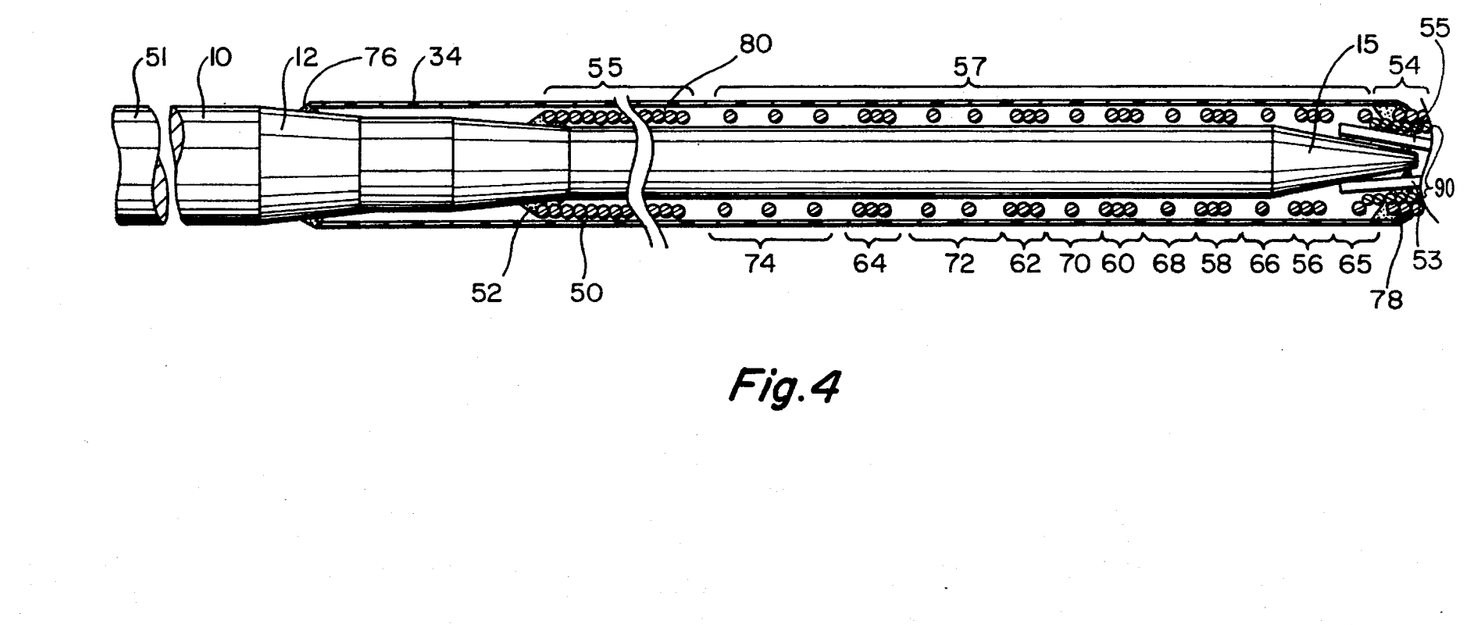
FIG. 4 is a longitudinal sectional fragmented illustration of a variation to the third embodiment of the invention.

Referring to FIG. 4, inner coil 90 is attached at its distal end to the hemispherical tip weld 22 and may be attached at its proximal end to the forming wires 53 and 55 and the tapered segment 15, preferably by adhesive. Alternatively, the proximal end of the inner coil may not be attached to any element. Besides inner coil 90, the embodiment of FIG. 4 is identical to that of FIG. 3. The inner coil 90 preferably has an outer diameter within the range of 0.006–0.012 inches, a length within the range of 1–4 cm, and is made from a radiopaque material such as platinum, gold or a platinum/gold alloy. The diameter of the wire from which the inner coil is wound is preferably within the range of 0.001 to 0.003 inches. The inner coil 90 is surrounded by the distal section of the coil 50 such that the distal section will appear highly radiopaque.

Figure 5:
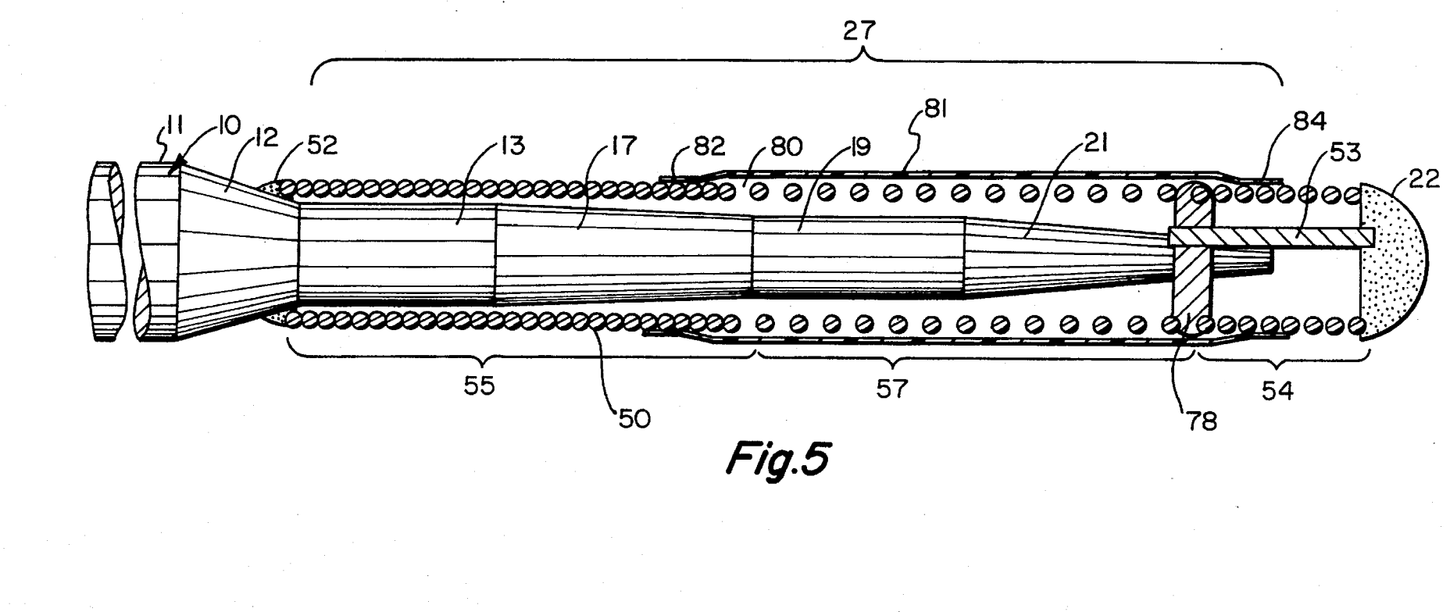
FIG. 5 is a longitudinal sectional fragmented illustration of a fourth embodiment of the invention.

FIG. 5 shows a fourth embodiment of the invention in which the guidewire preferably falls within the range of 180–300 cm in length and includes an elongated rotationally rigid, longitudinally flexible core wire 10, preferably made of stainless steel. The majority of the length (preferably 110–280 cm) of the core wire is in the proximal portion 11 which has a substantially uniform diameter, typically within the range of 10–18 mils. The proximal portion 11 merges into a first tapered segment 12, preferably 2–10 cm in length, which, in turn, merges into a first barrel segment 13, preferably 10–20 cm in length. The diameter of barrel segment 13 preferably is within the range of 5–12 mils, less than that of proximal portion 11. First barrel segment 13 merges into a second tapered segment 17, preferably 2–6 cm in length, which, in turn, merges into a second barrel segment 19, preferably 5–15 cm in length. The diameter of barrel segment 19 preferably is within the range of 4–10 mils, less than that of first barrel segment 13. Barrel segment 19 merges into a third tapered segment 21, preferably 2–10 cm in length, which extends to the distal end of the core wire.

One or more forming wires (only one of the forming wires 53 is shown) extend from tapered segment 21 to a rounded tip weld 22. The forming wires, typically one to five cm in length, preferably are adhesively attached to tapered segment 21 at joint 78 and extend approximately 2 cm beyond the distal tip of core wire 10. Alternatively, joint 78 can be soldered or brazed. The forming wires preferably are made from a specially treated precipitation hardenable alloy material. One such material is an alloy of nickel, cobalt, molybdenum and chromium, commercially available from Fort Wayne Metals of Fort Wayne, Ind. under the trade designation MP35N. Another suitable material is a single stage martensitic precipitation hardenable stainless steel having modified proportions of chromium and nickel and with additional elements of copper and titanium, commercially available from Carpenter Steel Co. of Reading, Pa. under the trade designation 455PH. Still another suitable material is a precipitation hardenable alloy that is commercially available from Sandvik Steel under the trade designation Sandvik 1RK91.

While the distal region 27 of the core wire has been shown and described herein as including two tapered segments, two barrel segments and two forming wires, it should be understood that other core wires can be used with this fourth embodiment such as, for example, a core wire that has a distal region including only a single barrel segment which merges into a tapered segment that extends to the distal end of the core wire (with or without forming wires). Any of the guidewire embodiments disclosed herein can be practiced with a core wire having a distal region that either includes one or more forming wires or, alternatively, a core wire that extends to the distal tip of the guidewire.

A radiopaque coil 50 is supported by and attached to the distal region 27 of the core wire 10. The distal end of the coil 50 is attached by the hemispherical tip weld. Just proximally of the distal end of coil 50, the coil is attached to the core wire at joint 78. Joint 78 also adds integrity to the structure of the distal end of the guidewire to prevent the coil 50 from separating from the core wire if the forming wires break during use. The coil extends proximally to the tapered section 12 of the core wire 10. The proximal end of the coil is attached to the core wire by adhesive at joint 52. Alternatively, joint 52 can be soldered or brazed. Spring 50 preferably is formed from a radiopaque material such as platinum/gold or other suitable alloy. The diameter of the wire from which the coil is wound preferably is within the range of 0.0015–0.003 inches. The outer diameter of the coil preferably is within the range of 0.010–0.018 inches. A typical coil length falls within the range of 15–40 cm. While the coil is shown in FIG. 5 as having an outer diameter that is less than that of the proximal portion 11 of the core wire, it is to be appreciated that the outer diameter of the coil is preferably equal to or approximately equal to the outer diameter of the proximal portion 11 of the core wire.

Spring 50 has varying pitch along its length including distal and proximal tightly wound coil sections 54 and 55 separated by an intermediate loosely wound window coil section 57. The tightly wound coil sections appear dark under fluoroscopy and the loosely wound window coil section appears light. Distal section 54 preferably falls within the range of one to five cm in length, proximal section 55 preferably falls within the range of 10–25 cm in length, and intermediate window section 57 preferably falls within the range of 5–20 cm in length.

Intermediate window section 57 may include a number of short tightly wound coil sections (not shown) separated by loosely wound coil sections as in the embodiment of FIG. 3. The tightly wound sections appear as dark markers under fluoroscopy for providing reference lengths and location marks for a physician. The number of markers and the length and spacing thereof can be selected to suit a particular application.

Intermediate window section 57 of the coil 50 is covered by a flexible polymeric sleeve 81. The sleeve 81 is kink resistant and includes a lubricious surface for aiding in guidewire maneuverability. The sleeve preferably is formed from polyethylene terephthalate (PET) but may be formed from other thermoplastic polymers such as polyethelene. A hydrophilic or hydrophobic coating may be used to coat the outer surface of the guidewire including the polymer sleeve for added lubricity.

The sleeve preferably is as thin as is practical, depending on the polymer material from which the sleeve is made, in order that the region of the sleeve displays a desired degree of flexibility. The wall thickness of the sleeve preferably falls within the range of 0.0002–0.002 inches. The sleeve 81 is attached to the guidewire only at its proximal and distal ends 82 and 84 (each preferably within the range of 0.5–2 cm in length) by heat shrinking the sleeve only at those ends. Only the ends 82 and 84 of the sleeve 81 are respectively heat shrunk about the tightly wound coils of the proximal 55 and distal 54 regions immediately adjacent the window section 57.

A small gap 80 exists between the outer surface of the intermediate section 57 of coil 50 and the inner surface of sleeve 81. The size of the gap is approximately equal to 0.0001 inches but would depend on the thickness of the sleeve wall and the outer diameter of the spring. The gap prevents the contour of the outer surface of the coils from projecting through the sleeve and contacting the inner arterial wall (which would occur if the sleeve were heat shrunk about the entire length of the coil) so that the guidewire can be navigated smoothly through the artery during use. Additionally, the sleeve 81 insulates the loosely wound coils of the intermediate section 57 from the inner arterial wall to prevent them from significant movement relative to one another during advancement through an artery. Such movement could result in altering the fluoroscopic image of the guidewire and/or altering the structure and functionality of the coils of the spring.

The distal region of the fourth embodiment (FIG. 5) of the guidewire thus has distal tip and proximal sections that are highly radiopaque and an intermediate section that is lightly radiopaque. Such an arrangement is referred to as "black/grey/black" (from the proximal section to the distal end), referring to its relative appearance under fluoroscopy. The highly radiopaque distal segment provides clear, visible fluoroscopic indication of the distal tip of the guidewire to indicate clearly the guidewire position. Typically, the distal tip of the guidewire is advanced through and beyond the stenosis to be treated. The intermediate, lightly radiopaque segment is intended to be disposed at the region of the stenosis so that the region will not be materially obstructed by radiopaque effects of the guidewire. Thus, the full radiopaque effect of the radiopaque contrast liquid injected into the artery can be visualized on the fluoroscope, particularly in the critical stenosed region of the artery. The radiopaque proximal segment provides an indication of the position and configuration of the more proximally located portions of the guidewire and, therefore, the proximal arterial anatomy, so that a physician can observe the more proximally located portions of the guidewire.

The proximal and distal sections of the coil preferably are equally highly radiopaque. Alternatively, the distal section can be more radiopaque than the proximal section. To achieve the desired relative radiopacity, the distal section 54 of the coil may be plated with a radiopaque material.

The guidewire of the present invention provides a number of advantages. The guidewire facilitates better lesion assessment both by providing a non-obstructing region that does not impair fluoroscopic evaluation of the shape of the lesion and by providing a radiopaque proximal section that allows visualization of the proximal portion of the wire. It also provides radiopaque markers which offer a simple means by which the physician can determine the length of the lesion, adjacent arterial dimensions, and/or reference lesion or stent location. Selection of an appropriately sized balloon and, if necessary, selection of an appropriate stent is, therefore, facilitated. Additionally, the sleeve provides a uniform outer diameter to the distal region of the guidewire to ensure smooth movement of the catheter during advancement. Also, as in the fourth embodiment, by heat shrinking the sleeve only at its ends, the outer contour of the coils is prevented from projecting through the sleeve, and the sleeve insulates the loosely wound coils from the inner arterial wall, preventing them from substantial relative movement.

Thus, we have described a guidewire having varied degrees of radiopacity whereby, a distal section of the distal region of the guidewire appears dark under fluoroscopy and an intermediate section of the distal region appears generally white (or light in an alternate embodiment). At least one radiopaque marker may be located in the intermediate section for providing reference lengths and location marks for a physician. A polymer sleeve encases at least part of the distal region, providing a uniform outer diameter to the region (in some embodiments), to aid in smooth catheter advancement. It should be understood, however, that the foregoing description of the invention is intended merely to be illustrative thereof and that other embodiments and modifications may be apparent to those skilled in the art without departing from its objects, purposes and spirit.

Having thus described the invention, what we desire to claim is:

1. A guidewire comprising:

an elongate flexible shaft;

a distal radiopaque coil supported about and attached to a distal portion of the shaft;

a proximal radiopaque coil supported about and attached to an intermediate portion of the shaft, the proximal coil being longitudinally spaced from the distal coil; and a polymer sleeve encasing the shaft between the proximal and distal coils and at least a portion of the proximal and distal coils.

2. A guidewire as defined in claim 1, wherein the polymer sleeve encases a proximal region of the distal coil and a distal region of the proximal coil.

3. A guidewire as set forth in claim 1 further comprising at least one radiopaque marker attached to the shaft between the distal and proximal coils, the at least one marker being encased by the polymer sleeve.

4. A guidewire as set forth in claim 3 wherein the at least one marker includes at least one radiopaque marker band attached to the shaft.

5. A guidewire as set forth in claim 1 wherein the distal coil is more radiopaque than the proximal coil such that the distal coil will appear darker than the proximal coil under fluoroscopy.

6. A guidewire as set forth in claim 5 wherein the wire from which the distal coil is wound has a greater diameter than the wire from which the proximal coil is wound.

7. A guidewire as set forth in claim 1 wherein the radiopacity of the distal coil is approximately equal to the radiopacity of the proximal coil such that both coils will appear equally dark under fluoroscopy.

8. A guidewire comprising:

an elongate flexible shaft;

a radiopaque coil supported by and attached to a distal portion of the shaft;

at least one radiopaque marker attached to an intermediate portion of the shaft, proximally to the coil; and a polymer sleeve attached to the shaft and encasing the at least one marker such that a gap exists between the at least one marker and the sleeve.

9. A guidewire as set forth in claim 8 wherein the at least one marker includes at least one marker band attached to the shaft.

10. A guidewire as set forth in claim 9 wherein the polymer sleeve also encases the shaft proximally to the at least one marker band.

11. A guidewire as set forth in claim 10 wherein the polymer sleeve also encases the proximal end of the coil.

* * * * *